United States Patent
Roe et al.

(10) Patent No.: US 10,245,187 B2
(45) Date of Patent: Apr. 2, 2019

(54) WAISTBAND FOR AN ABSORBENT ARTICLE

(71) Applicant: The Procter & Gamble Company, Cincinnati, OH (US)

(72) Inventors: Donald Carroll Roe, West Chester, OH (US); Michael Dale Trennepohl, Cincinnati, OH (US)

(73) Assignee: The Procter & Gamble Plaza, Cincinnati, OH (US)

( * ) Notice: Subject to any disclaimer, the term of this patent is extended or adjusted under 35 U.S.C. 154(b) by 655 days.

(21) Appl. No.: 14/964,652

(22) Filed: Dec. 10, 2015

(65) Prior Publication Data

US 2016/0089273 A1  Mar. 31, 2016

Related U.S. Application Data (63) Continuation of application No. 13/172,095, filed on Jun. 29, 2011, now Pat. No. 9,241,841.

(51) Int. Cl.
  *A61F 13/15*   (2006.01)
  *A61F 13/49*   (2006.01)

(52) U.S. Cl.
  CPC .. *A61F 13/15585* (2013.01); *A61F 13/15593* (2013.01); *A61F 13/49011* (2013.01)

(58) Field of Classification Search
  USPC ............. 156/229, 307.1, 307.3, 308.2, 308.4
  See application file for complete search history.

(56) References Cited

U.S. PATENT DOCUMENTS

| | | |
|---|---|---|
| 4,515,595 A | 5/1985 | Kievit et al. |
| 5,151,092 A | 9/1992 | Buell et al. |
| 5,531,730 A * | 7/1996 | Dreier ............... A61F 13/49009 604/385.19 |
| 5,669,996 A * | 9/1997 | Jessup ............... A61F 13/15601 156/163 |
| 6,120,487 A | 9/2000 | Ashton |
| 6,428,524 B1 | 8/2002 | Johansson et al. |
| 7,727,217 B2 | 6/2010 | Hancock-Cooke |

(Continued)

FOREIGN PATENT DOCUMENTS

| | | |
|---|---|---|
| EP | 1 117 530 B1 | 11/2005 |
| EP | 0 376 022 B2 | 3/2006 |

(Continued)

OTHER PUBLICATIONS

An Introduction to Kraton Polymers Structure Chemistry Performance, by Kraton Polymers U.S. LLC, dated May 15, 2008, 16 pages.

(Continued)

*Primary Examiner* — Sing P Chan
(74) *Attorney, Agent, or Firm* — Andrew J. Hagerty; Sarah M. DeCristofaro (57) ABSTRACT

A waistband for an absorbent article having a waistband with differential extensibility and/or contraction along the circumference of the waist opening. The waistband may provide a uniform appearance along the circumference of the waist opening. The waistband may have a central zone and at least two outboard zones. The outboard zones of the waistband may be less contracted than the central zone, when the absorbent article is in a relaxed state.

7 Claims, 5 Drawing Sheets

(56) References Cited

U.S. PATENT DOCUMENTS

| | | |
|---|---|---|
| 2002/0007164 A1 | 1/2002 | Boggs et al. |
| 2005/0107764 A1 | 5/2005 | Matsuda et al. |
| 2006/0025737 A1 | 2/2006 | Song et al. |
| 2008/0132872 A1 | 6/2008 | Trennepohl |
| 2010/0217218 A1 | 8/2010 | Bäck et al. |
| 2011/0072561 A1 | 3/2011 | Kinoshita et al. |
| 2011/0178489 A1 | 7/2011 | Baba et al. |
| 2011/0245794 A1 | 10/2011 | Hermansson |

FOREIGN PATENT DOCUMENTS

| | | |
|---|---|---|
| JP | 03-024003 | 5/1996 |
| WO | WO 2004/047699 | 6/2004 |
| WO | WO 2007/024327 | 3/2007 |
| WO | WO 2010/032581 | 3/2010 |
| WO | WO 2010/076690 | 7/2010 |
| WO | WO 2010/076691 | 7/2010 |

OTHER PUBLICATIONS

PCT International Search Report, 10 pages, dated Oct. 24, 2012.

\* cited by examiner

WAISTBAND FOR AN ABSORBENT ARTICLE

CROSS REFERENCE TO RELATED APPLICATION

This application is a Continuation of application Ser. No. 13/172,095, filed on Jun. 29, 2011, which is incorporated herein by reference.

FIELD

A waistband for an absorbent article is disclosed, more particularly, a waistband for an absorbent article having zones of elasticity.

BACKGROUND

Absorbent articles can be worn around or near the body to contain exudes, such as urine, fecal matter, menses, sweat, blood, and the like. Absorbent articles for the containment of urine, fecal matter, or menses, in particular, may be shaped generally like underwear, in that the absorbent articles may have a waist opening and leg openings. For various reasons, purchasers of absorbent articles may prefer that the absorbent articles look and fit like underwear. For example, some users of absorbent articles may prefer to keep their incontinence or menstrual cycle private, and prefer absorbent articles which look like underwear to maintain discretion. Some users of absorbent articles may prefer the aesthetic appearance of underwear to the aesthetic appearance of absorbent articles. Some users, such as wearers or their caregivers, of absorbent articles may associate the appearance of underwear with common functional aspects of underwear, such as breathability, stretch, and skin feel. Absorbent articles that fit like underwear may be or may be perceived as being more comfortable, less prone to leakage, and more discreet.

It can be difficult to make an absorbent article look and fit like underwear, particularly if the absorbent article is of piecemeal construction. That is, while underwear may be constructed from a handful of components, such as a fabric and a few kinds of elastic, absorbent articles may be constructed from a dozen or even dozens of different components. One of the portions of an absorbent article that may be distinct in appearance and fit from underwear is the waist opening. While underwear may have a circumferentially continuous waistband with elastic properties encircling the wearer's waist, some absorbent articles, such as taped diapers, may have an open-waist structure that is closed when the absorbent article is applied to the wearer. The closure of an absorbent article may involve adhesives or mechanical fasteners, and may not have the same properties along the entire circumference of the waist opening. For example, an absorbent article may have an elastic waist feature only in the back waist region, or only in the front waist region.

While it is possible to add a continuous waistband around the entire waist opening of an absorbent article, doing so has drawbacks. For example, if the waistband is closed, it is no longer possible to provide a taped diaper configuration, which may be preferred by some users. If the waistband is left open and applied as a taped diaper, the elastic properties of the waistband may cause the laterally outboard edges of the waist opening to contract, which may make it difficult to apply the absorbent article to a wearer. If the waistband is applied to only portions of the waist opening, the piecemeal construction of the absorbent article may be evident, which may highlight the differences between the absorbent article and underwear, rather than downplaying the differences between the absorbent article and underwear.

There remains a need for an absorbent article having the appearance of a circumferentially continuous waistband, which provides elastic properties at desired locations, and maintains the ease of application of a taped diaper configuration.

SUMMARY

In some aspects of the present disclosure, an absorbent article may comprise a longitudinal centerline and a waistband. The waistband may comprise a central zone centered around the longitudinal centerline. A waistband may comprise an outboard zone disposed laterally outboard of the central zone on each side of the central zone. The outboard zone may contract less than the central zone when the absorbent article is in a relaxed state. The central zone and the outboard zone may each have an applied elongation. The applied elongation of the central zone may be greater than the applied elongation of the outboard zone. The central zone may have an applied elongation of between 25% and 35%. The outboard zone may have an elastic elongation of between 0% and 10%. There may be a gradient of applied elongation in the waistband outboard from a longitudinal centerline. The central zone and the outboard zone may be color-matched when viewing the garment-facing surface of the waistband. The central zone and the outboard zone may have the same lateral dimensions. The central zone may comprise an elastic material. The outboard zone may comprise an elastic material. The elastic material in the outboard zone, if present, may be the same as the elastic material in the central zone, if present. The elastic material in the central zone may be contracted when the absorbent article is in a relaxed state. The elastic material in the outboard zone may be uncontracted when the absorbent article is in a relaxed state. The absorbent article may be a diaper, or a pull-on diaper, or a taped diaper.

In some aspects of the present disclosure, a waistband may comprise a central zone and an outboard zone laterally outboard of the central zone. The central zone and the outboard zone may each have an installed elongation. The installed elongation of the central zone may be greater than the installed elongation of the outboard zone. The installed elongation of the central zone may be between 25% and 35%. The installed elongation of the outboard zone may be between 0% and 10%. There may be a gradient of installed elongation in the waistband outboard from a longitudinal centerline.

In some aspects of the present disclosure, a method for making a waistband may comprise elongating a central portion of an elastic material. The method may comprise elongating an outboard portion of the elastic material to a lesser degree than the central portion. The method may comprise affixing the elastic material to another material with the central portion elongated and the outboard portion elongated to a lesser degree. The method may comprise allowing the central portion of the elastic material to relax. The method may thereby create a laminate with a contracted central portion. The outboard portion of the elastic material might not be elongated. The method may comprise treating the outboard portion of the elastic to render it inelastic. The method may comprise shirring, gathering, or pleating material in an outboard zone of the laminate to create rugosities. The method may comprise applying a separate, discrete waistband layer to an absorbent article. The method may comprise allowing the outboard portion of the elastic material to relax, thereby creating a laminate with contracted central and outboard portions.

In some aspects of the present disclosure, a method of making a waistband may include: elongating a central portion of an elastic material; elongating an outboard portion of the elastic material to a lesser degree than the central portion; affixing the elastic material to another material with the central portion elongated and the outboard portion elongated to a lesser degree to form a waistband; allowing the central portion of the elastic material to relax, thereby creating a laminate with a contracted central portion; and applying the waistband to an absorbent article.

In some aspects of the present disclosure, a method of making a waistband may include: elongating a central portion of an elastic material; elongating an outboard portion of the elastic material to a lesser degree than the central portion; affixing the elastic material to another material with the central portion elongated and the outboard portion elongated to a lesser degree to form a waistband; allowing the central portion of the elastic material to relax, thereby creating a laminate with a contracted central portion; and applying the waistband to an absorbent article, wherein the central zone and the outboard zone each has an installed elongation, and the installed elongation of the central zone is greater than the installed elongation of the outboard zone, and wherein the central zone has an installed elongation of between 25% and 35%, and the outboard zone has an installed elongation of between 0% and 10%.

DETAILED DESCRIPTION

As used herein, the terms "elastic" and "elastomeric" refer to any material that, upon application of a biasing force, can stretch to an elongated length of at least about 110% of its relaxed, original length (i.e. can stretch to 10 percent), without rupture or breakage, and upon release of the applied force, recovers at least about 40% of its elongation. For example, a material that has an initial length of 100 mm can extend at least to 110 mm, and upon removal of the force would retract to a length of 106 mm (40% recovery). The term "inelastic" refers herein to any material that does not fall within the definition of "elastic" above. "Elastic" may refer to a single material, or it may refer to a combination of materials making up a laminate or a macrostructure in an article. An elastic material may be incorporated into a laminate or macrostructure which is not elastic, or which is less elastic than one or more of the elastic materials of the laminate or macrostructure.

As used herein, the term "elastic modulus" refers to Young's Modulus, or tensile stress divided by tensile strain, where tensile stress is tensile force divided by area of cross-section of the test material and tensile strain is the extension of the material divided by the original length of the material. For webs having a large width-to-thickness ratio, such as 50:1 or greater, the tensile stress may be reported in terms of the tensile force divided by the width of the sample.

As used herein, the term "elastic elongation" refers to the percent strain at the force wall, as measured using the test method described herein.

As used herein, the term "absorbent article" refers to devices which absorb and contain body exudes and, more specifically, refers to devices which are placed against or in proximity to the body of the wearer to absorb and contain the various exudes discharged from the body. Exemplary absorbent articles include diapers; training pants; pull-on diapers (i.e., a diaper having a pre-formed waist opening and leg openings such as illustrated in U.S. Pat. No. 6,120,487); a refastenable diapers or pull-on diapers; incontinence briefs and undergarments; diaper holders and liners; feminine hygiene garments, such as sanitary napkins and panty liners; and the like. Absorbent articles may be disposable or reusable. Some absorbent articles may have disposable components and reusable components. For example, an absorbent article may have a reusable outer cover and a disposable absorbent insert. The discussion below refers to an absorbent article in the form of a diaper, however, it should be understood that the discussion would also apply to any other form of absorbent article having a waist opening, unless otherwise noted.

As used herein, the term "color-matched" describes two or more discrete elements of an absorbent article, each having a color, when said colors are contained within a specified CIELab color space volume. Ideally, the imparted colors of at least two surfaces of discrete elements will occupy a CIELab color space volume of less than about 190. The visible surfaces are analyzed according to the Test Method described below. Upon analysis, the inherent color of an element comprising a visible surface will yield $L^*$, $a^*$, and $b^*$ coordinates. The CIELab color space volume (V), for a first color ($L^*1$, $a^*1$, $b^*1$) and a second color ($L^*2$, $a^*2$, $b^*2$), is calculated according to the following formula:

$$V = \frac{4}{3}\pi \left| \frac{\Delta L^*}{2} \right| \left| \frac{\Delta a^*}{2} \right| \left| \frac{\Delta b^*}{2} \right|.$$

Within the formula, $\Delta L^*$ is the difference in $L^*$ values between the two colors and is calculated by: $\Delta L^* = L^*2 - L^*1$. The $\Delta a^*$ is the difference in $a^*$ values between the two colors and is calculated by: $\Delta a^* = a^*2 - a^*1$. The $\Delta b^*$ is the difference in $b^*$ values between the two colors and is calculated by: $\Delta b^* = b^*2 - b^*1$. The CIELab color space system and measurements are described in greater detail in, for example, U.S. Patent Application Publication No. 2006/0025737 to Song, et al.

As used herein, the terms "inboard" and "outboard" refer to the position of an object relative to the longitudinal or lateral centerline of an absorbent article or a component of an absorbent article. A first object is inboard of a second object if the first object is nearer the longitudinal or lateral centerline than the second object. A first object is outboard of a second object if the first object is farther from the longitudinal or lateral centerline than the second object.

As used herein, the term "pre-stretch" describes a material which is incorporated into an article or garment in a tensioned, extended state, such that the material tends to contract when the tension is released. "Pre-stretch" can be quantified as the amount of extension of the pre-stretch material at the time it is incorporated into the article or garment relative to its unextended or relaxed length.

As used herein, the term "waist" describes generally the region of a garment or article which sits near or upon a wearer's natural waist, which is the smallest part (in circumference) of the indentation between the hips and the ribcage.

As used herein, the term "waist edge" describes the longitudinal edge(s) of a garment or article at or nearest the wearer's natural waist.

As used herein, the term "waistband" describes a feature of a garment or article at or near the waist edge of the garment or article. The waistband may be functional. For example, the waistband may comprise one or more elastic members to hold the waist region of the article against the wearer's body to prevent gapping and/or leakage. As another example, the waistband may provide sustained fit at the waist, as, for example, when the weight of the article changes as it is loaded with body exudes. The waistband may also be aesthetic, for example, a feature defined by color, shape, size, pattern, or other characteristic. The waistband will generally lie at the waist edge, however, in some embodiments, the waistband may lie below the waist edge, for example, if the waist edge extends above the wearer's natural waist and the waistband lies at the wearer's natural waist, or to position the waistband more directly in a line of tension between fastening elements in a taped diaper context. (Providing a waistband in the line of tension may result in a higher in-use tension in the waistband.) Unless otherwise noted, the term "waistband" refers to the waistband as it is incorporated into an absorbent article, and should be considered in the context of the article. That is, the waistband is not examined or tested independent of the construction of the article of which it is a part. This is not to exclude testing of the assembled waistband of an absorbent article that has been severed from the remainder of the absorbent article, i.e., from components or portions outside the waistband, which may include at least portions of the absorbent core, leg cuffs, crotch portion, etc.

As used herein, the term "waistband component" refers to one or more elements of a waistband prior to incorporation into a garment or article. For example, an elastic band may be a waistband component, which may be incorporated into a waistband.

As used herein, the term "relaxed state" refers to a material when there are no external tensile forces acting upon the material. Similarly, "relaxed state" refers to an article composed of two or more materials when there are no external tensile forces acting upon the article. An article in a "relaxed state" may comprise materials under tension because of connection(s) to other materials in the article. Thus, an article in a "relaxed state" may include contracted and uncontracted portions.

As used herein, the term "wearer-facing" refers to the surface of an article or a component of an article which would face the wearer when an article is applied to a wearer as intended for normal use. The term "garment-facing" refers to the surface of an article or a component of an article opposite the wearer-facing side, and, if a garment is worn over the article, nearest the garment when the article is applied to a wearer as intended for normal use.

Figure 1:
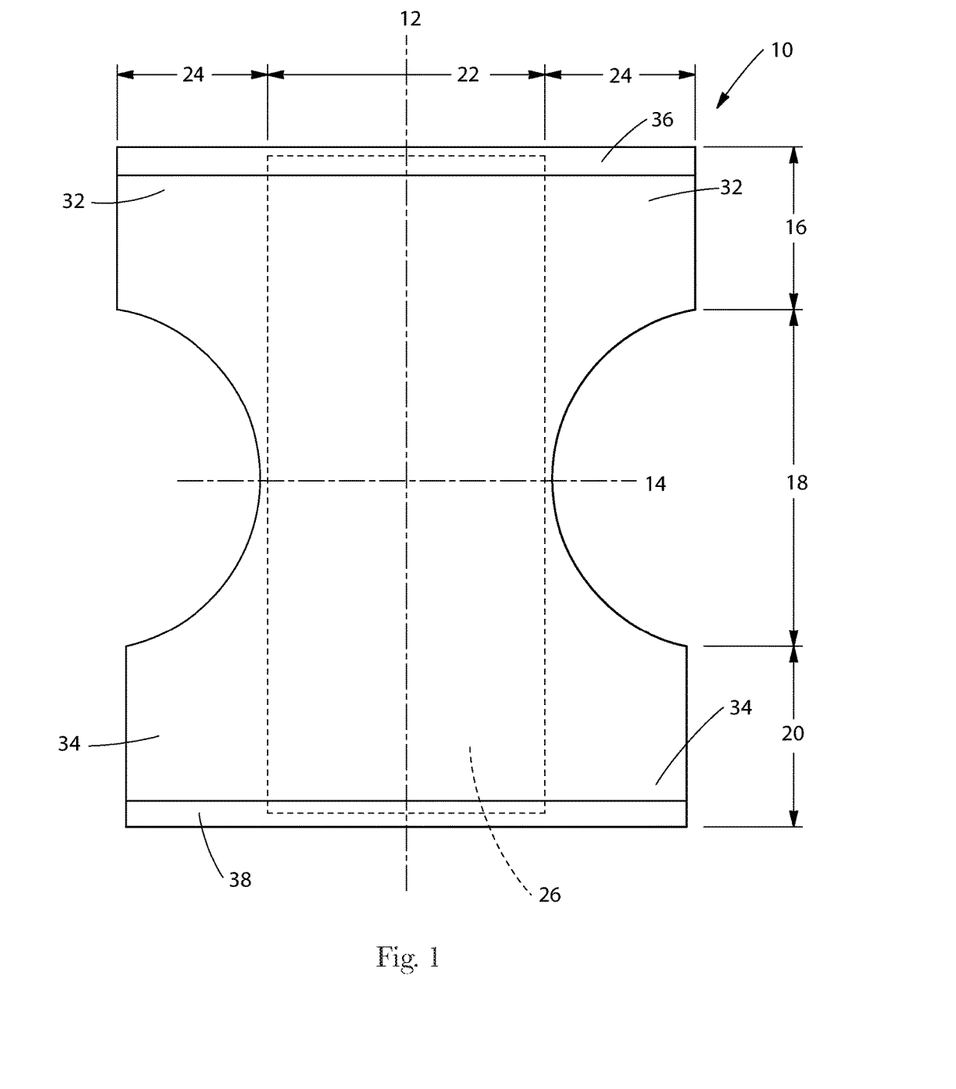
FIG. 1 is a schematic plan view of an exemplary absorbent article.
Figure 2:
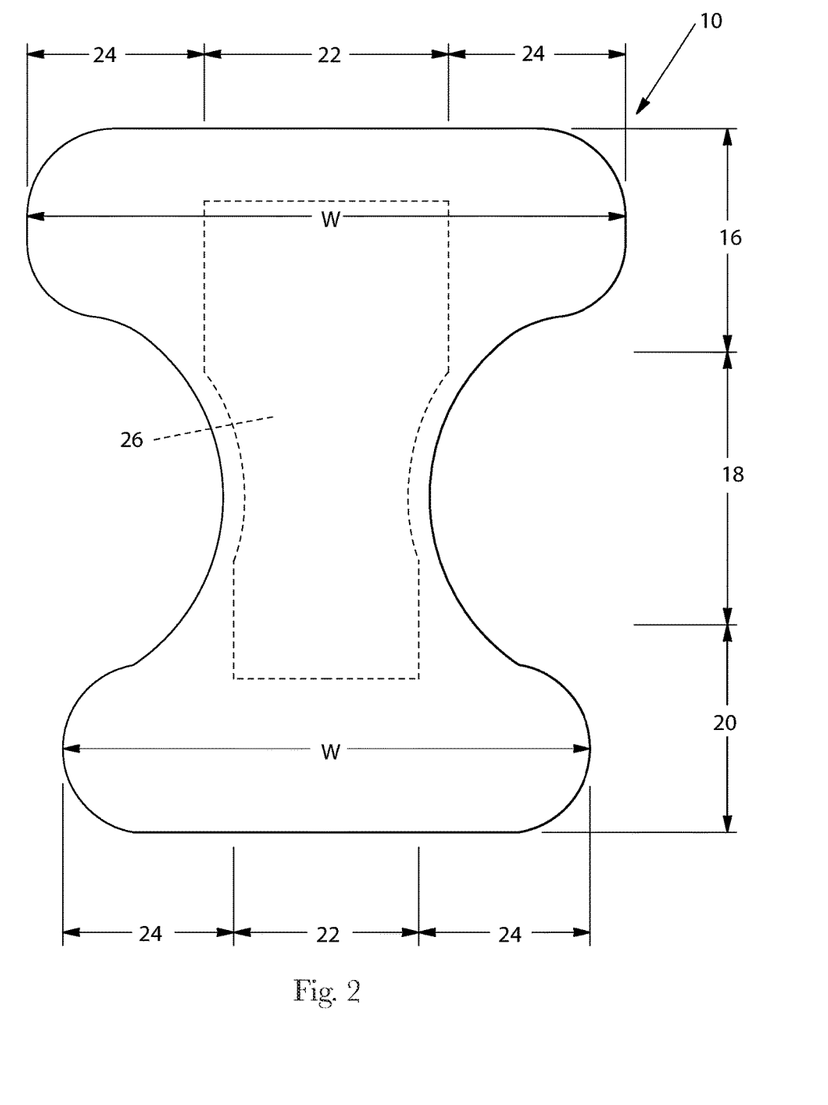
FIG. 2 is a schematic plan view of an exemplary absorbent article.

FIG. 1 shows an exemplary absorbent article 10 having longitudinal centerline 12 and lateral centerline 14. Absorbent article 10 has rear waist portion 16 and front waist portion 20, which are connected longitudinally by crotch portion 18. Each of rear waist portion 16 and front waist portion 20 has a central zone 22, centered around longitudinal centerline 12, and outboard zones 24 laterally outboard of central zone 22. The lateral width of central zone 22 may correspond roughly to the lateral width of absorbent core 26, if present, or to the narrowest width of absorbent article 10 across crotch portion 18, and may be about 80% or less, or about 50% or less, of the lateral width of the corresponding rear waist portion 16 or front waist portion 20. The central zone 22 of rear waist portion 16 may have the same dimensions as, or different dimensions than, the central zone 22 of front waist portion 20. Outboard zones 24 may correspond roughly to the lateral width of the corresponding rear ears 32 or front ears 34, if present. (The ears may also be referred to as side panels.) Outboard zones 24 each may be about 10%, or 20%, or 25%, or 30%, or 35%, or more of the lateral width of the corresponding rear waist portion 16 or front waist portion 20, and may be less than 50%, or less than 40%, or less than 33%, or less than 25%, of the lateral width of the corresponding rear waist portion 16 or front waist portion 20. As shown in FIG. 2, if the ears do not have uniform, straight edges, the width W of the waist portion is measured at the widest point. As also shown in FIG. 2, absorbent article 10 may have different dimensions for central zone 22 and outboard zones 24 in front portion 20 and rear portion 16 of an article.

Rear waistband 36 and front waistband 38, if both are present, are disposed longitudinally opposite one another. Rear waistband 36, front waistband 38, or both may be formed at least in part by materials continuous with other parts of absorbent article 10, such as a backsheet, topsheet, or ears, or may be separate, discrete parts that are joined to absorbent article 10. The waistband(s) may be disposed on the garment-facing surface or the wearer-facing surface of the article, or may be disposed between any of the layers of the article. Regardless of whether they are integral or discrete or where they are located, rear waistband 36, front waistband 38, or both may appear to be continuous with other parts of absorbent article 10. For example, the waistbands may be formed of the same material as other components of the absorbent article, or may have color, or a pattern, or both, which match other components of the absorbent article. In some embodiments, the waistbands are color-matched to other components of the absorbent article, such as ears 32 or 34, or topsheet 40, or backsheet 42. The color-matched components may be a color other than white, for example, pink, blue, red, green, yellow, purple, orange, brown or black. In some embodiments, the waistbands have a distinct appearance relative to other components of the absorbent article. For example, the waistbands may have a contrasting, aesthetically complementary color or pattern relative to other components of the absorbent article. Rear waistband 36 and front waistband 38 may be similar in appearance to contribute to an impression of a circumferentially continuous, underwear-like waistband.

FIG. 1 shows rear ears 32 and front ears 34, however, in some embodiments, a single ear panel may extend laterally between rear waist region 16 and front waist region 20. In some embodiments, absorbent article 10 may have no rear ears, or no front ears. The ears, if present, may be formed at least in part by materials continuous with other parts of absorbent article 10, such as a backsheet or topsheet, or may be separate, discrete parts that are joined to absorbent article 10. The ears, if present, may be joined to form a pull-on diaper, or may include fasteners for securing a taped diaper about the waist of a wearer. The fasteners may be of any suitable sort, including adhesives, cohesives, and mechanical fasteners. Suitable mechanical fasteners may include, but are not limited to, hook and loop, hook and hook, buttons, snaps, ties, zippers, and the like. Front waist region 20 may include a landing zone for receiving a fastener, or may be constructed of a material generally suitable for receiving a fastener. For example, front waist region 20 may be constructed from, or may include a landing zone constructed from, a material suitable as an adherend for an adherent fastener, or a loop material suitable for receiving a hook fastener. In some embodiments, the fastening system is refastenable. In some pull-on diapers, the ears are removably and/or refastenably joined. In such embodiments, the pre-joined ears may include fasteners for refastening the ears, that is, for reclosing the waist opening. Such a configuration may be helpful, for example, if the ear joints are disrupted to check to see if the diaper has been soiled, or for adjusting the attachment of the ears for better fit on a wearer.

If the ears are prejoined, it may be possible to provide a circumferentially continuous elastic element in the waistband. However, if the prejoined ears are designed to enable removal and refastening, or if the ears are not prejoined, as in a taped diaper which is in an open-waist configuration when beginning to apply the diaper to a wearer, a circumferentially continuous elastic element may complicate the application of the diaper to a wearer. For example, a tensioned elastic element extending through outboard zones 24 may cause the laterally outboard portion of the ears to curl inward, toward the wearer-facing surface of the diaper. When applying a taped diaper, the diaper may be laid flat, and the wearer may be positioned on top of the taped diaper. If the laterally outboard portion of rear ears 32 has curled inward, the wearer may be laying on the rear ears 32, making it difficult to locate and manipulate rear ears 32 to close the waist opening around the wearer. Similarly, if a pull-on diaper is opened, curled edges may make it difficult to reposition or refasten the ears.

The laterally outboard edges of the diaper may be more manageable if the properties of the central zone 22 and outboard zones 24 of the waistband are varied. In some embodiments, the elastic modulus of the waistband in the central zone 22 is less than the elastic modulus of the waistband in the outboard zones 24, and in other embodiments the elastic modulus of the waistband in the central zone 22 is greater than the elastic modulus of the waistband in the outboard zones 24.

Embodiments wherein the elastic modulus of the waistband in the central zone is less than the elastic modulus in the outboard zones may be desirable for users who tend not to apply a significant tensile force to the fasteners during application, but who nonetheless desire the rear waist portion 16 of the diaper 10 to be held against the skin of the wearer to prevent leakage, such as BM leakage, from the rear waist portion. The lower application force generated by these users may preferentially elastically extend the central portion of the waistband, allowing it to hold the waist region of the article against the wearer's body during wearing. The elastic modulus of the central zone 22 can be made lower than that of the outboard zone 24 in a number of ways. For example, the central zone 22 may comprise fewer elastic strands or elastic strands with a smaller cross-sectional area than the elastic strands in outboard zone 24. Or the basis weight of an elastic film in the central zone 22 may be lower than the basis weight of an elastic film in the outboard zone 24.

Conversely, embodiments wherein the elastic modulus of the waistband in the outboard zones 24 is less than the elastic modulus in the central zone 22 may be desirable for users who tend to apply a significantly greater tensile force to the fasteners during application, and who desire a customized fit, i.e., a caregiver may actively adapt the diaper to the wearer during the application process. The application force generated by these users may preferentially elastically extend the outboard portions of the waistband, allowing a caregiver to extend them more easily to accommodate the wearer's specific geometry. The elastic modulus of the outboard zones 24 can be made lower than that of the central zone 22 in a number of ways. For example, the outboard zones 24 may comprise fewer elastic strands or elastic strands with a smaller cross-sectional area than the elastic strands in central zone 22. Or the basis weight of an elastic film in the outboard zones 24 may be lower than the basis weight of an elastic film in the central zone 22.

In some embodiments, the amount of pre-stretch in the central zone 22 is greater than the amount of pre-stretch in the outboard zones 24. The amount of pre-stretch may be such that central zone 22 is contracted, or the portion of central zone 22 comprising a pre-stretch element may be contracted, and outboard zones 24 are not contracted, or outboard zones 24 may be contracted to a lesser degree than central zone 22. In some embodiments, central zone 22 includes an elastic element and outboard zones 24 do not include an elastic element. In some embodiments, central zone 22 and outboard zones 24 include an elastic element, and the elastic element of outboard zones 24 has been deactivated. For example, the elastic element of outboard zones 24 may be treated, as with heat, mechanical activation, or chemicals, to stiffen the elastic element or otherwise impair the elasticity of the elastic element. As another example, the elastic element of outboard zones 24 may be secured to another layer of absorbent article 10 which is inelastic, or which is less elastic than the elastic element of outboard zones 24, such that the elastic element of outboard zones 24 cannot extend beyond the extensibility of the inelastic material to which it is secured. The elastic material of outboard zones 24 may be joined to another layer or component of absorbent article 10 having a stiffness sufficient to reduce or eliminate the elastic extensibility of the elastic material of outboard zones 24. By limiting the elasticity of outboard zone 24 relative to central zone 22, outboard zone 24 may contract, in a relaxed state, to a lesser degree than central zone 22. A lesser degree of contraction in outboard zone 24 may help reduce the tendency of outboard zone 24 to curl or roll in on itself, or to be foreshortened to an extent inconvenient for the user. That is, outboard zones 24 may contract less than central zone 22 when absorbent article 10 is in a relaxed state.

It may be desirable to provide less pre-stretch in the outboard zones 24, relative to the central zone 22, of both the rear waistband 36 and the front waistband 38. However, it is not necessary that the structures of rear waistband 36 and front waistband 38 are the same. For example, rear waistband 36 may have a central zone 22 with greater pre-stretch than outboard zones 24, while front waistband 38 may have uniform pre-stretch across the central zone 22 and outboard zones 24. As another example, rear waistband 36 may have a central zone 22 with a higher elastic modulus than outboard zones 24, and front waistband 38 may have a central zone 22 with an elastomeric element and outboard zones 24 with no elastomeric element. Put another way, the construction of the rear waistband 36 may be selected independent of the construction of the front waistband 38. Thus, the embodiments described herein may be used for a rear waistband 36, a front waistband 38, or both.

A waistband may have a greater elastic elongation in the central zone 22 than in the outboard zone 24. For example, the central zone may have an elastic elongation between about 25% and 35%, or between 10% and 50%, and the outboard zone 24 may have an elastic elongation between 0% and 10%, or between 0% and 25%. That is, outboard zone 24 may be inelastic, as defined herein. There may be a gradient of elastic elongation from the longitudinal centerline 12 of the central zone 22 in a lateral outboard direction, where the elastic elongation is greatest at the longitudinal centerline 12 of the central zone 22. The gradient may be continuous or discontinuous. For example, a continuous gradient may have a more or less continuous reduction in elastic elongation from the center of the central zone 22 in a laterally outboard direction. In contrast, a discontinuous gradient may have three or more discrete steps, where the elastic elongation is approximately consistent within each step, and each step has a higher elastic elongation than the next laterally outboard step. To balance competing desires for fit and ease of application, the central zone 22 may be between about 20% and about 70% of the width of the waistband, and the outboard zones 24 combined (that is, the combined length of each outboard zone 24 on either side of the central zone 22) may be between about 80% and about 30% of the length of the waistband. In some embodiments, the width of central zone 22 may be as small as about 20 mm. In some embodiments, a very small width of central zone 22 may still provide some benefits in terms of reducing gapping and sustaining fit. In some embodiments, the central zone 22 and the outboard zone 24 have the same lateral dimensions, that is, the central zone 22 and the outboard zone 24 are each about 50% of the width of the waistband.

In some embodiments, a waistband component 50 is constructed by stretching an elastic material 44 and, while elastic material 44 is in a stretched state, bonding elastic material 44 to at least one precursor web 48 in such a manner that, when tension is released on the resulting composite waistband component 50, the entire waistband component contracts. As shown in FIGS. 3A-3F, elastic material 44 may have a first, relaxed length 45, and a second, extended length 46. The second, extended length does not need to be, but may be, a fully extended length. Elastic material 44 may be applied at its second, extended length 46 to precursor web 48 while precursor web 48 is in a relaxed state, or is under tension sufficient to reduce slack in precursor web 48 without extending precursor web 48. When elastic material 44 is allowed to relax, the waistband component 50 comprising elastic material 44 and precursor web 48 will contract to approximately the first, relaxed length 45 of elastic material 44 (with some variance based on the elastic recovery of elastic material 44 from its second, extended length 46 and because the finite bending stiffness of the joined materials may prevent full contraction). Gathers or pleats 54 may be formed in waistband component 50.

Figure 3A:
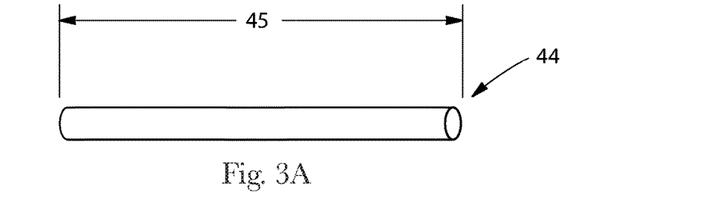
FIG. 3A is a plan view of an exemplary elastic material.
Figure 3B:
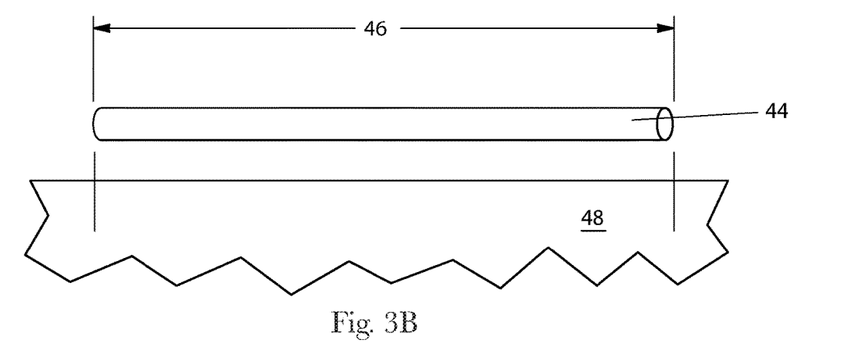
FIG. 3B is a plan view of an exemplary elastic material with a partial view of a web precursor.
Figure 3C:
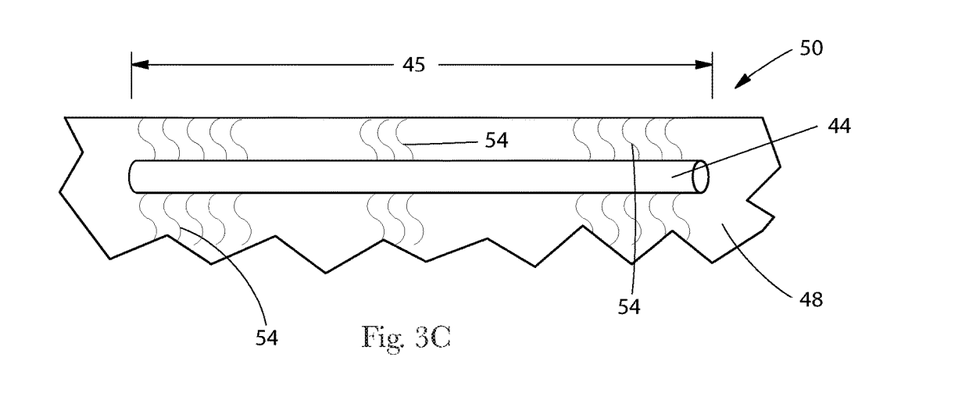
FIG. 3C is a partial plan view of an exemplary waistband component.
Figure 3D:
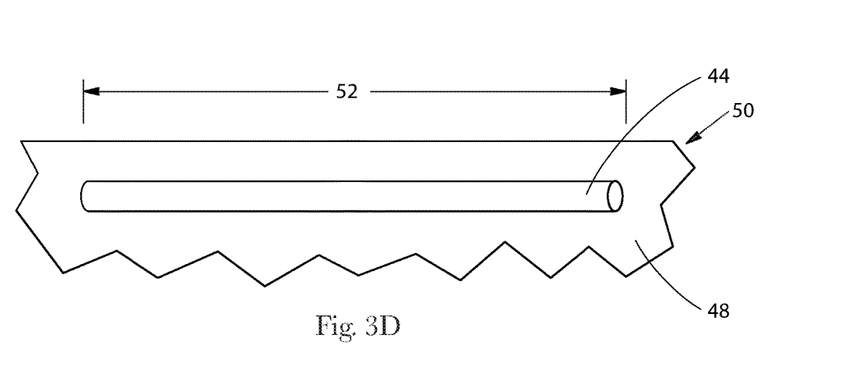
FIG. 3D is a partial plan view of an exemplary waistband component in an extended state.
Figure 3E:
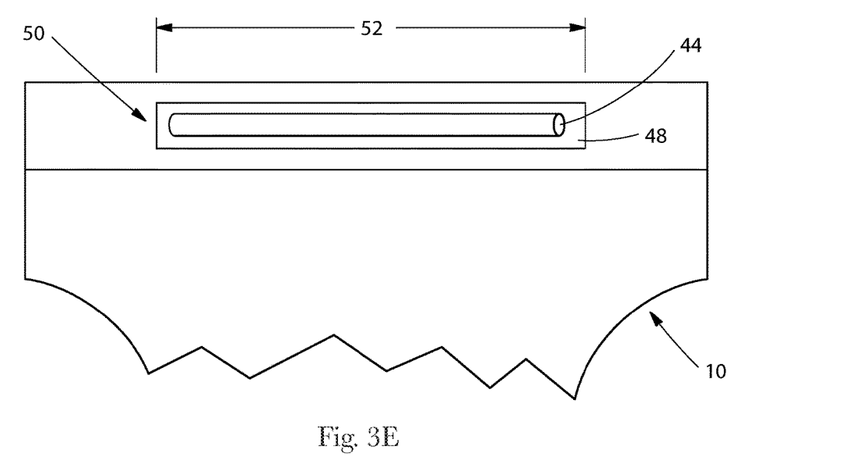
FIG. 3E is a plan view of an exemplary waistband component in an extended state with a partial view of an absorbent article.
Figure 3F:
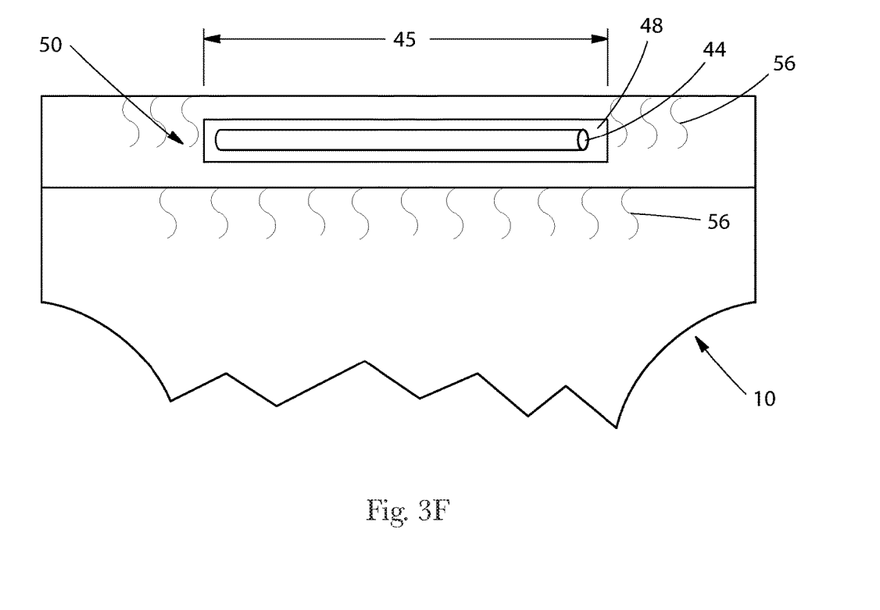
FIG. 3F is a plan view of an exemplary waistband component in a relaxed state with a partial view of an absorbent article.

Waistband component 50 may be extended from its first, relaxed length 45 to a second, extended length 52. Extended length 52 may be the same as or different than the second, extended length 46 of elastic material 44. Waistband component 50 may be applied in its second, extended length 52 to absorbent article 10. When waistband component 50 is allowed to relax, the absorbent article comprising waistband component 50 may contract to approximately the first, relaxed length 45 of waistband component 50 (with some variance expected, as described above). Gathers or pleats 56 may be formed in or adjacent to waistband 36 or 38 of absorbent article 10, as shown in FIG. 3F. FIG. 3F shows waistband component 50 applied to topsheet 40 of absorbent article 10, however, as described above, waistband component 50 may be applied to other components of absorbent article 10, such as backsheet 42, or may be sandwiched between different layers comprising absorbent article 10, such as between topsheet 40 and backsheet 42.

Precursor web or webs 48 may comprise nonwovens, films, or composites thereof, and may each, for example, have a basis weight in the range of 10 gsm to 30 gsm. If more than one precursor web 48 is present, the webs may be the same or different in composition, form (i.e., woven, nonwoven, films, etc.), and basis weight. Elastic material 44 may comprise an elastomeric film or one or more elastomeric strands or ribbons. The relative amount that elastic material 44 is stretched prior to combining to form waistband component 50 may be referred to as "installed elongation". For example, if the first, relaxed dimension 45 of elastic material 44 is 100 mm and elastic material 44 is stretched by 75 mm to a second, extended length 46 of 175 mm prior to combining elastic material 44 with precursor web 48 to form waistband component 50, the installed elongation is 75%.

The installed elongation may be different than the applied elongation of waistband component 50 to the garment or article 10. The "applied elongation" refers to the relative amount waistband component 50 is stretched versus its first, relaxed dimension 45 prior to bonding or affixing it to the garment or article 10. For example, if a piece of the waistband component 50 as described above, having a 75% installed elongation, has a first, relaxed dimension 45 of 100 mm and is elongated 35 mm prior to attachment to a garment or article 10, the waistband 36 or 38 has an applied elongation of 35%. The relative amount of contraction this waistband will cause in the region of the garment to which it is affixed may vary, depending on the relative stiffness of the garment. If the garment is very flexible in the waistband region, the amount of contraction may approach 35%. However, if the garment is very stiff in that region, the amount of contraction of the garment may be significantly less than 35%.

In some embodiments, elastic material 44 is added directly to a garment or article 10 with no intermediate waistband component 50 being formed. For example, a disposable absorbent article 10 having a topsheet 40 and a backsheet 42 may be formed, in part, by placing the topsheet 40 and the backsheet 42 adjacent to one another. Elastic material 44 may be applied in a second, extended length 46 between the topsheet 40 and the backsheet 42, as described above. In these embodiments, the applied and installed elongation may be considered to be the same, or, in the alternative, because no intermediate waistband component 50 independent of the disposable absorbent article 10 is formed, there is no installed elongation to be measured and the waistband 36 or 38 has only an applied elongation.

In some embodiments, the waistband 36 or 38 may have zones having different applied elongations. For example, a waistband component 50 may be stretched to different percent strain values along the length of the waistband component 50, such that the applied elongation varies along the length of the assembled waistband 36 or 38. In some embodiments, one or more portions of the waistband component 50 may be unstretched or unextended, creating waistband zones with no applied elongation. As another example, different waistband components 50 having different installed elongations may be used to construct various zones in the waistband 36 or 38, such as outboard zones 24 and central zones 22. In some embodiments, one or more of the waistband components 50 used to construct a waistband 36 or 38 having different zones may be inelastic, creating waistband zones with no applied elongation.

In some embodiments, the elastic material 44 comprises Lycra strands and the precursor webs 48 comprise spunbond polypropylene nonwovens. The Lycra strands may have a decitex of between about 500 and 1600, typically between about 680 and 1100. The waistband component 50 may comprise any number of strands at any spacing. For example, the waistband component 50 may comprise between 2 and 5 strands per centimeter of the waistband dimension generally orthogonal to the Lycra strands. The waistband component 50 may have an installed elongation of between about 50% and about 300%, or between about 75% and about 200%. The waistband 36 or 38 may have an applied elongation of between about 0% and 100%, or between about 10% and 50%, or between 25% and 35%.

Although the construction and/or materials of the central zone 22 and the outboard zone 24 may differ, e.g., in type of materials or in elastic structure to vary the elastic properties of the different zones, it may be desirable for the waistband 36 or 38 to have a circumferentially continuous appearance. For example, the central zone 22 and outboard zones 24 may be color-matched, to enhance a perception of continuity and/or minimize visual distinctions between the central zone 22 and outboard zones 24. In some embodiments, the waistband 36 or 38 has consistent rugosities along the entire length of the waistband 36 or 38. In some embodiments, waistbands 36 and 38 have consistent rugosities, and in some embodiments, there are consistent rugosities along the entire waist opening of article 10. That is, ears 32 and 34, if present, may have rugosities consistent with waistbands 36 and 38. As non-limiting examples, shirring, pleating, or gathering may be used to create rugosities in the waistband. The rugosities may be measured in number of rugosities per centimeter (density), and average length in the longitudinal direction (height). If the waistband includes elastic zones, the rugosities may be arranged to match the elastic segment or zones. For example, inelastic zones of the waistband may be shined to create rugosities of a similar height and density to the rugosities formed by the elastic component or components of the elastic zone of the waistband. Rugosities may also be used to disguise differences in elasticity over different zones of the waistband. For example, if the central zone 22 has a greater pre-stretch than the outboard zone 24, the outboard zone 24 may be shirred, pleated, or gathered to create rugosities similar in appearance (e.g., having a similar height and density) to the rugosities created by the elastic components of the central zone 22.

In some embodiments, a separate, distinct layer is applied over the waistband to create a circumferentially continuous waistband at least in an outer layer. In some embodiments, a distinct waistband is created by printing a solid color or a repeating pattern circumferentially along the waistband, to hide or reduce the visibility of differences in the waistband structure.

A waistband as described herein can be made, for example, by providing an elastic material, elongating a central portion of the elastic material, affixing the elastic material with the central portion elongated to another material, and allowing the central portion of the elastic material to relax, thereby creating a laminate with a contracted central portion. The laterally outboard portion of the elastic material may be elongated to a lesser degree than the central portion. The outboard portion of the elastic material may not be elongated. The outboard portion of the elastic material may be elongated at least to the same degree of the central portion, and the outboard portion of the elastic material treated to set the elastic material, such that it is no longer elastically elongatable. The outboard portion of the elastic material may be elongated until it is set and is no longer elastically elongatable, that is, it may be plastically elongated. A separate, distinct cover layer may be applied over the waistband to create the appearance of a circumferentially continuous waistband. The outboard zone of the waistband may be shined, gathered, or pleated to create rugosities. The height and density of the rugosities may be matched to the rugosities, if any, created in the central zone by the elastic material. The elastic material may be, for example, in the form of bands, scrims, films, nets, or combinations of these.

Test Methods

Simple Tensile Test for Force Wall

The materials described herein, when pulled in a Tensile Test, may show two distinct regions: the first region in which the main contribution to the force is from an elastic portion of a laminate and a second region in which the force contribution from an inelastic portion of the laminate becomes significant. In the force versus strain curve, the second region has a significantly higher slope compared to the first region. The percent strain at which this change in slope occurs is referred to as the Force Wall. Some materials do not show two distinct regions, making it impossible to consistently identify a Force Wall; such materials are outside the scope of the claimed invention.

The Simple Tensile Test for Force Wall utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The test is performed under laboratory conditions of 23° C.±2° C. and relative humidity of 50%±2%. The samples are conditioned for 24 hours prior to testing.

Test Protocol

1. Select a sample that is 7.62 cm long and 1.5 cm wide, with the long dimension being in the direction of stretch. If a waist or leg band sample is taken from a product, the width of the sample should be the entire width of the waist or the leg band. In some cases, if it is not be possible to get a 7.62 cm long sample, a smaller sample may be used, but a gauge length of 25 mm must still be used.
2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.
3. Calibrate the tester according to the manufacturer's instructions.
4. Set the distance between the upper and lower grips at 25 mm.
5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.

6. Pull the sample at a constant cross head speed of 254 mm/min to 1000% strain (i.e., 11× the $l_{ini}$), or until the sample breaks.
7. The computer records the force exerted on the sample during the test as a function of applied strain.
8. Plot force (N/cm) versus percent strain and measure the force wall as the strain at which the slope of the force vs. strain curve increases sharply. This can either be done manually or using the software of the tensile tester. The modulus is the slope of the curve prior to the force wall.
9. Perform 5 repetitions on each material to be tested and report average and standard deviation for each material.

Contraction

Contraction of a zone is measured relative to an assembled article. Measure the length of the zone when the assembled article is in a relaxed state. Grasp the ends of the zone, for example, the central zone, in the grips of a tensile tester and apply 5N of force. Measure the length of the zone at 5N of force (this measurement may be available from software associated with the tensile tester, or may be measured manually). If the absorbent article or zone fails (breaks or pulls apart) at 5N of force or less, use instead the length at the maximum force the article can withstand. Calculate the contraction as 100%×(length of the zone under tension−length of the zone when the article is in a relaxed state)/(length of the zone under tension).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making the waistband, comprising:
   elongating a central portion of an elastic material;
   elongating an outboard portion of the elastic material;
   affixing the elastic material to another material with the central portion elongated and the outboard portion elongated to form a waistband component;
   allowing the central portion of the elastic material to relax, thereby creating a waistband component laminate with a contracted central portion; and
   applying the waistband component laminate to an absorbent article comprising:
      a rear waist portion comprising a rear waistband comprising a topsheet layer and a backsheet layer;
      a front waist portion opposite the rear waist portion; and
      a crotch portion longitudinally connecting the rear waist portion and the front waist portion;
   wherein the waistband component laminate is applied to the rear waist portion so that gathers are formed in the topsheet layer and/or the backsheet layer within the rear waist portion;
   wherein an applied percent elongation of the central portion is greater than that of the outboard portion.

2. The method of claim 1,
   wherein each of the rear waist portion and the front waist portion comprise a central zone centered around a longitudinal centerline, a first outboard zone, and a second outboard zone opposite the first outboard zone, wherein each of the first outboard zone and the second outboard zone extend laterally outboard from the central zone;
   a first rear ear extending laterally outboard from the central zone, wherein a lateral width of the first rear ear corresponds to the first outboard zone; and
   a second rear ear extending laterally outboard from the central zone and opposite the first rear ear, wherein a lateral width of the second rear ear corresponds to the second outboard zone.

3. The method of claim 2, wherein the waistband component laminate extends from the first outboard zone, across the central zone, and into the second outboard zone, wherein a first portion of the waistband component laminate is disposed on the first rear ear and a second portion of the waistband component laminate is disposed on the second rear ear, and a third portion of the waistband component laminate is disposed on the central zone.

4. The method of claim 3, wherein the third portion of the waistband component laminate, the second portion of the waistband component laminate, and the first portion of the waistband component laminate each has an applied elongation, and the applied elongation of the third portion is greater than the applied elongation of at least one of the first portion and the second portion.

5. The method of claim 1, comprising treating the outboard portion of the elastic to render it inelastic.

6. The method of claim 1, further comprising shirring, gathering, or pleating material in an outboard zone of the waistband component laminate to create rugosities.

7. The method of claim 1,
   wherein the central zone has an installed elongation of between 25% and 35%, and the outboard zone has an installed elongation of between 0% and 10%.

* * * * *